United States Patent
Jurczyk et al.

(10) Patent No.: US 7,972,803 B2
(45) Date of Patent: Jul. 5, 2011

(54) CENTROSOMAL PROTEINS AND SECRETION

(75) Inventors: Agata Jurczyk, Shrewsbury, MA (US); Rita Bellis Bortell, Shirley, MA (US); Aldo A. Rossini, Sudbury, MA (US); Stephen J. Doxsey, Princeton, MA (US)

(73) Assignee: University of Massachusetts, Boston, MA (US)

( * ) Notice: Subject to any disclaimer, the term of this patent is extended or adjusted under 35 U.S.C. 154(b) by 126 days.

(21) Appl. No.: 11/985,545

(22) Filed: Nov. 15, 2007

(65) Prior Publication Data

US 2009/0029935 A1 Jan. 29, 2009

Related U.S. Application Data

(60) Provisional application No. 60/859,383, filed on Nov. 15, 2006.

(51) Int. Cl.
G01N 33/567 (2006.01)
C12Q 1/68 (2006.01)
C12N 5/00 (2006.01)
C12N 5/02 (2006.01)

(52) U.S. Cl. ............... 435/7.21; 435/6; 435/325
(58) Field of Classification Search .......... 435/7.21, 435/6, 325
See application file for complete search history.

(56) References Cited

U.S. PATENT DOCUMENTS

| | | |
|---|---|---|
| 2004/0175721 A1 | 9/2004 | Doxsey |
| 2005/0208058 A1 | 9/2005 | Doxsey et al. |
| 2006/0160762 A1 | 7/2006 | Zetter et al. |
| 2006/0167106 A1 | 7/2006 | Zhang et al. |

OTHER PUBLICATIONS

Mikule et al., "Loss of centrosome integrity induces p38-p53-p21-dependent G1-S arrest," *Nature Cell Biology*, 9(2):160-170 and S1-S7 (2007).
Sillibourne et al., "Chromatin remodeling proteins interact with pericentrin to regulate centrosome integrity," *Molecular Biology of the Cell*, 18:3667-3680 (2007).
Zimmerman et al., "Mitosis-specific anchoring of gamma tubulin complexes by pericentrin controls spindle organization and mitotic entry," *Molecular Biology of the Cell*, 15:3642-2657 (2004).
Buchanan et al, "Preptin derived from proinsulin-like growth factor II (proIGF-II) is secreted from pancreatic islet beta-cells and enhances insulin secretion," *Biochem J.*, 360(Pt 2):431-439 (2001).
Doxsey et al., "Pericentrin, a highly conserved centrosome protein involved in microtubule organization," *Cell*, 76(4):639-650 (1994).
Flory and Davis, "The centrosomal proteins pericentrin and kendrin are encoded by alternatively spliced products of one gene," *Genomics*, 82:401-405 (2003).
Gromley et al., "Centriolin anchoring of exocyst and SNARE complexes at the midbody is required for secretory-vesicle-mediated abscission," *Cell*, 123(1):75-87 (2005).
Gromley et al., "A novel human protein of the maternal centriole is required for the final stages of cytokinesis and entry into S phase," *J. Cell. Biol.*, 161(3):535-545 (2003).
Jurczyk et al., "Pericentrin forms a complex with intraflagellar transport proteins and polycystin-2 and is required for primary cilia assembly," *J. Cell. Biol.*, 166(5):637-643 (2004).
Khodjakov and Rieder, "The sudden recruitment of gamma-tubulin to the centrosome at the onset of mitosis and its dynamic exchange throughout the cell cycle, do not require microtubules," *J. Cell. Biol.*, 146(3):585-596 (1999).
Mikule et al., "Loss of centrosome integrity induces p38-p53-p21-dependent G1-S arrest," *Nature Cell Biology*, 9(2):160-170 (2007).
Miyazaki et al., "Establishment of a pancreatic beta cell line that retains glucose-inducible insulin secretion: special reference to expression of glucose transporter isoforms," *Endocrinology*, 127(1):126-132 (1990).
Miyoshi et al., "Characterization of pericentrin isoforms in vivo," *Biochem. Biophys. Res. Comm.* 351:745-749 (2006).
Oakley and Oakley, "Identification of gamma-tubulin, a new member of the tubulin superfamily encoded by mipA gene of *Aspergillus nidulans*," *Nature*, 338(6217):662-664 (1989).
Purohit et al., "Direct interaction of pericentrin with cytoplasmic dynein light intermediate chain contributes to mitotic spindle organization," *J. Cell. Biol.*, 147:481-491 (1999).
Tsuboi et al., "Mammalian exocyst complex is required for the docking step of insulin vesicle exocytosis," *J. Biol. Cell.*, 280(27):25565-25570 (2005).
Zimmerman et al., "Mitosis-specific anchoring of gamma tubulin complexes by pericentrin controls spindle organization and mitotic entry," *Mol. Biol. Cell.*, 15:3642-3657 (2004).
Eglen, "High throughput screening, high content screening, primary and stem cells new techniques now converging," *Drug Discovery World*, Spring 2009:25-31 (2009).
Jurczyk et al., "A novel role for the centrosomal protein, pericentrin, in regulation of insulin secretory vesicle docking in mouse pancreatic β-cells," *PLoS ONE*, 5(7):e11812. doi:10.1371/journal.pone.0011812 (2010).
Ovcharenko et al., "High-throughput RNAi screening in vitro: From cell lines to primary cells," *RNA*, 11:985-993 (2005).

*Primary Examiner* — Thaian N Ton
(74) *Attorney, Agent, or Firm* — Fish & Richardson P.C.

(57) ABSTRACT

Described are methods for modulating cellular secretion, and methods for identifying novel modulators of cellular secretion, that target centrosomal proteins.

23 Claims, 8 Drawing Sheets
(8 of 8 Drawing Sheet(s) Filed in Color)

```
                              SEQUENCE LISTING

<160> NUMBER OF SEQ ID NOS: 26

<210> SEQ ID NO 1
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 1
gcagcugagc ugaaggaga                                                     19

<210> SEQ ID NO 2
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 2
gguucuggaa acaacuggg                                                     19

<210> SEQ ID NO 3
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 3
agucggcaga gcacuguga                                                     19

<210> SEQ ID NO 4
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 4
ugaccgcaag gacgucuuu                                                     19

<210> SEQ ID NO 5
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 5
ucucguacuc cagaagacu                                                     19

<210> SEQ ID NO 6
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 6
aagagaagca gaugcugca                                                     19
```

```
<210> SEQ ID NO 7
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 7
acuucgccug guccaacuu                                                19

<210> SEQ ID NO 8
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 8
ucuauccgaa agcccaguc                                                19

<210> SEQ ID NO 9
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 9
gucccccaaa cagagaaac                                                19

<210> SEQ ID NO 10
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 10
ucagcuucgu gauucucag                                                19

<210> SEQ ID NO 11
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 11
agggaaccaa ggaaaggca                                                19

<210> SEQ ID NO 12
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 12
gagcaaaagc aggagaucc                                                19

<210> SEQ ID NO 13
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 13
```

```
gcacaguaaa uacccacua                                                    19

<210> SEQ ID NO 14
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 14
gcaaaugcug ccuuccuug                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 15
ccagagauga gccuaccag                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 16
gagaugccag cagcagaug                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 17
acagagaacg auggugcca                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 18
ucaggaaaca ggugagcag                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 19
ggaucagaga cucuaccuu                                                    19

<210> SEQ ID NO 20
<211> LENGTH: 19
<212> TYPE: RNA
<213> ORGANISM: Artificial Sequence
```

```
<220> FEATURE:
<223> OTHER INFORMATION: Synthetic siRNA

<400> SEQUENCE: 20
gugcugcagc agacauuac                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 21
uaugagcauu gaggcagag                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 22
cugucacuca agccaagga                                                    19

<210> SEQ ID NO 23
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 23
gcagagagau uuagagauuu u                                                 21

<210> SEQ ID NO 24
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 24
ggaaagagau cauggagaau u                                                 21

<210> SEQ ID NO 25
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 25
ggagagagaa ggagcgagau u                                                 21

<210> SEQ ID NO 26
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 26
uuggaacagc ugcagcaga                                                    19
```

CENTROSOMAL PROTEINS AND SECRETION

CLAIM OF PRIORITY

This application claims the benefit of U.S. Provisional Patent Application Ser. No. 60/859,383, filed on Nov. 15, 2006, the entire contents of which are hereby incorporated by reference.

FEDERALLY SPONSORED RESEARCH OR DEVELOPMENT

This invention was made with Government support under Grant No. 5T32 DK007302 awarded by the National Institutes of Health. The Government has certain rights in the invention.

TECHNICAL FIELD

This invention relates to methods for modulating secretion, e.g., insulin secretion.

BACKGROUND

Centrosomes are composed of two centrioles and pericentriolar material, including centrosomal proteins. Centrosomes are known to play a role in cell division and microtubule nucleation, and may also be involved in cytokinesis completion (Gromley et al, J Cell Biol. 2003 May 12; 161(3): 535-45. Epub 2003 May 5; US PGPub No. 2005/0208058) and membrane trafficking; centrosomal proteins are required for secretory vesicle mediated cytokinesis (Gromley et al., Cell. 2005 Oct. 7; 123(1):75-87).

The centrosome of vertebrate cells and its yeast equivalent, the spindle pole body, have been well recognized as microtubule organizing centers (MTOC) in eukaryotic cells. Centrosomes play an important role in nucleating and organizing of microtubules in interphase and forming the mitotic spindle necessary for proper segregation of DNA during mitosis. More recently, centrosome proteins have been shown to provide a molecular 'scaffold' to enable cell polarization and to localize proteins involved in certain signaling pathways. In addition, centrosome proteins comprise the structural underpinning for formation of the primary cilium, an organelle that 'senses' the cellular milieu (Jurczyk et al., J. Cell. Biol. 166 (5):637-43 (2004). In each case, these diverse functions derive from a concentrated confluence of centrosome proteins at a single cytosolic location. However, it is little appreciated that fully half of the total centrosome protein is more diffusely distributed within the cytosol, yet its exact localization and functional importance there is not understood.

The centrosome is a structurally complex organelle consisting of two centrioles at right angles to each other, surrounded by the pericentriolar material (PCM). Numerous proteins have been identified in the centrosome, each with diverse functions implicating potential involvement in a multitude of cellular processes. Pericentrin and γ tubulin are integral centrosome proteins that play an important role in microtubule nucleation and organization, cell cycle progression and ciliogenesis (Doxsey et al., Cell. 76:639-650 (1994); Oakley and Oakley, Nature. 338(6217):662-4 (1989); Jurczyk et al., (2004) supra; Mikule et al., Nature Cell Biology. 9(2):160-170 (2007)). Pericentrin consists of multiple isoforms, three of which have been characterized: pericentrin B (360 kDa), pericentrin A (255 kDa), and pericentrin S (250 kDa) (Flory and Davis, Genomics. 82:401-5 (2003); Doxsey et al., (1994), supra; Miyoshi et al., Biochem. Biophys. Res. Comm. 351:745-749 (2006)). This large molecule interacts with numerous proteins and protein complexes including γ tubulin ring complex (Zimmerman et al., Mol. Biol. Cell. 15:3642-57 (2004)) and cytoplasmic dynein (Purohit et al., J. Cell. Biol. 147:481-491 (1999)). Gamma tubulin is indispensable for microtubule nucleation, and it is recruited to microtubule nucleating sites from the cytosol. Indeed, the centrosome pool of γ tubulin is freely exchangeable with the cytosolic pool, except for the fraction that associates with the centrioles (Khodiakov and Rieder, J. Cell. Biol. 146(3):585-96 (1999)).

SUMMARY

The present invention is based, at least in part, on the discovery that centrosomal proteins play a role in cellular secretion, e.g., insulin secretion.

Described herein are methods for identifying candidate modulators of cellular secretion. In one aspect, the methods include providing a sample comprising a centrosomal protein; contacting the sample with a test compound; and detecting binding of the test compound to the centrosomal protein. A test compound that binds to the centrosomal protein is a candidate modulator of secretion.

In some embodiments, the methods also include selecting a test compound on the basis that it binds to a centrosomal protein; providing a cell expressing the centrosomal protein, wherein the cell can undergo secretion, e.g., constitutive or stimulated secretion; contacting the cell with the test compound; and evaluating an effect of the test compound on secretion in the cell. A test compound that has an effect on secretion in the cell is an agent that modulates cellular secretion.

In another aspect, the methods include providing a cell expressing a centrosomal protein; contacting the cell with a test compound; and detecting an effect of the test compound on levels of expression of the centrosomal protein. A test compound that increases or decreases expression of the centrosomal protein is a candidate modulator of cellular secretion.

In yet a further aspect, the methods can include providing a cell expressing a reporter construct comprising a promoter region of a gene encoding a centrosomal protein linked to a reporter gene, such that expression of the reporter gene is indicative of expression driven by the promoter region; contacting the cell with a test compound; and detecting an effect of the test compound on levels of expression of the reporter gene. A test compound that increases or decreases expression of the reporter gene is a candidate modulator of cellular secretion.

In some embodiments, the methods can include selecting a test compound on the basis that it increases or decreases expression levels of a centrosomal protein; providing a cell expressing the centrosomal protein, wherein the cell can undergo secretion, e.g., constitutive or stimulated secretion; contacting the cell with the test compound; and evaluating an effect of the test compound on secretion in the cell, wherein a test compound that has an effect on secretion in the cell is an agent that modulates cellular secretion.

In some embodiments of the methods described herein, the test compound is a small molecule.

In another aspect, the invention provides methods for treating a disease characterized by reduced secretion in a subject, by administering to the subject, e.g., administering to the cells of the subject that are secreting abnormally or normally but insufficiently, a therapeutically effective amount of an inhibitory nucleic acid, e.g., an siRNA, shRNA, or antisense, targeting a centrosomal protein, to increase basal secretion levels.

In some embodiments of the methods described herein, the centrosomal protein is selected from the group consisting of pericentrin, centriolin, and gamma-tubulin.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

In FIGS. 1A-F, DNA staining is blue (DAPI), pericentrin immunostaining is green, and yellow shows overlay of pericentrin and red immunostaining as indicated.

FIG. 7A shows immunostaining of shScrambled treated cells with normal amount of pericentrin and insulin granules; FIGS. 7B and 7C show progressive loss of insulin in the pericentrin shRNA treated cells. GFP was co-expressed with the shRNA in order to visualize and sort the transduced cells. Pericentrin is in green, insulin in red, and DNA in blue. These results indicate that prolonged pericentrin knockdown causes total cessation of insulin production and de-differentiation of Min6 cells.

DETAILED DESCRIPTION

Figures 1A, 1B, 1C, 1D, 1E, 1F:
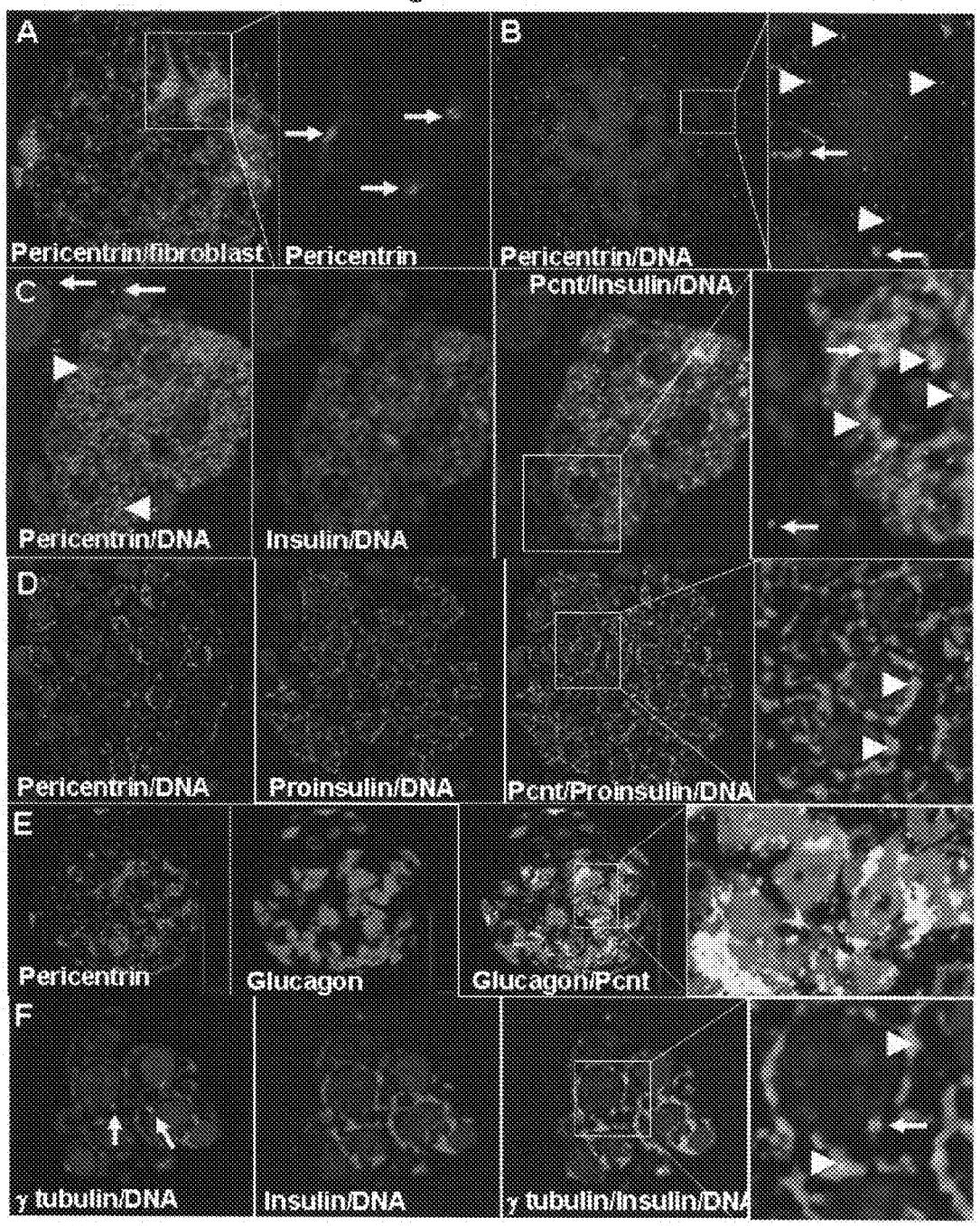
FIGS. 1A and 1B are each pairs of photomicrographs showing that pericentrin localizes to the centrosome (arrows) in primary fibroblast cells (pseudo-colored in red in 1A) and to the centrosome and granules (arrow heads in 1B) in the cytoplasm of isolated mouse pancreatic islets.
FIG. 1C is a set of four photomicrographs from mouse pancreas sections showing pericentrin (green) at centrosomes (arrows) of acinar cells (far left) and in islet cells (center). Pericentrin also localizes with insulin (red) in secretory granules (arrow heads).
FIG. 1D is a set of four photomicrographs of mouse pancreas sections showing immunostaining of pericentrin and proinsulin (red).
FIG. 1E is a set of four photomicrographs showing localization of pericentrin with glucagon secretory granules (red) in α cells of isolated pancreatic islets.
FIG. 1F is a set of four photomicrographs showing γ tubulin (red) localized to the centrosome (arrows) and granules (arrowheads) in the frequently used model for β cells MIN6 cells.

As described herein, the present inventors identified 'punctate' cytosolic immunostaining of centrosome protein in non-dividing, secretory pancreatic islet cells. It was hypothesized that centrosome protein in the cytosol may serve an additional, previously unrecognized role in protein secretion by directly interfacing with secretory vesicles. To test this hypothesis, the cellular localization and function of two major centrosome proteins, pericentrin and γ-tubulin, was investigated in pancreatic islet cells.

The present invention is based, at least in part, on the discovery of a novel centrosome function in controlling secretion, e.g., insulin secretion. Using multiple methods (e.g., immunofluorescence, electron microscopy, and cell fractionation) the present inventors showed that many centrosome proteins (including pericentrin, centriolin and gamma tubulin) co-localize with insulin granules in insulinoma cell lines as well as isolated mouse islets. As described herein, siRNA technology has been used to successfully knockdown the centrosome proteins; the results showed a progressive loss of intracellular insulin granules from beta cells, as well as hypersecretion of insulin into the media (in vitro) or plasma (in vivo) after the new insulin granules were re-synthesized (after about 30-60 minutes).

These results suggest a very important role for the centrosome proteins in maintaining proper insulin storage and regulation of insulin secretion. Since centrosome protein localization was not restricted to insulin secreting cells in pancreatic islets, but was also present in other secretory cells in the islets, it is reasonable to believe that centrosomal proteins are involved in all secretory events. This novel function of the centrosome provides a new target for drug development to treat diseases that are associated with abnormal secretion, such as diabetes, Huntington's Disease, Alzheimer's Disease, Polycystic Kidney Disease, Addison's Disease, Crohn's Disease, etc.

Centrosomal Proteins and Genes

A number of genes have been identified as playing important roles in the centrosomal apparatus of cells. Such genes are hereafter referred to as "centrosomal genes." Included among these are pericentrin, centriolin, δ-tubulin, ε-tubulin, γ-tubulin, GCP2, GCP3, GCP5, cNAP1, PCM1, NEK2, centrin2, CDC14A, CDC14B, gapcena, nemo, IKK1, and IKK2. Pericentriolar material (e.g., pericentrin) covers each centriole.

PCM1 refers to the gene encoding (or the gene product of) pericentriolar material 1, which, in humans, encodes transcript variants that include the transcript with GenBank Accession No. NM_006197. In some embodiments the PCM1 refers to an animal homolog of human PCM1.

Pericentrin A refers to the gene (or gene product of) PCNT1, which, in humans, encodes transcript variants that include the transcript with GenBank Accession No. NM_024844. In some embodiments the pericentrin A refers to an animal homolog of human pericentrin A.

Pericentrin B refers to the gene (or gene product of) PCNT2 which, in humans, encodes transcript variants that include the transcript with GenBank Accession No. NM_006031. In some embodiments the pericentrin B refers to an animal homolog of human pericentrin B. Pericentrin B is also known as kendrin.

γ-tubulin refers to the gene (or gene product of) TUBG1 which, in humans, encodes transcript variants that include the transcript with GenBank Accession No. NM_001070. In some embodiments the γ-tubulin refers to an animal homolog of human γ-tubulin.

δ-tubulin refers to the gene (or gene product of) TUBD1 which, in humans, encodes transcript variants that include the transcript with GenBank Accession No. NM_016261. In some embodiments the δ-tubulin refers to an animal homolog of human δ-tubulin.

ε-tubulin refers to the gene (or gene product of) TUBD1 which, in humans, encodes transcript variants that include the transcript with GenBank Accession No. NM_016262. In some embodiments the ε-tubulin refers to an animal homolog of human ε-tubulin.

GCP2 refers to the gene encoding (or gene product thereof) γ-tubulin complex 2 (homolog of yeast SPC97p) which, in humans, encodes transcript variants that include the transcript with GenBank Accession No. AF042378. In some embodiments GCP2 refers to an animal homolog of human GCP2.

GCP3 refers to the gene encoding (or gene product thereof) γ-tubulin complex 3 (homolog of yeast SPC98) which, in humans, encodes transcript variants that include the transcript with GenBank Accession No. AF042379. In some embodiments GCP3 refers to an animal homolog of human GCP3.

GCP5 refers to the gene encoding (or gene product thereof) tubulin gamma complex associated protein 5 (TUBGCP5), which, in humans, encodes transcript variants that include the transcript with GenBank Accession No. NM_052903. In some embodiments GCP2 refers to an animal homolog of human GCP5.

cNAP1 refers to the gene encoding (or gene product thereof) centrosomal Nek2-associated protein 1 described in Fry et al., J. Cell Biol., 141:1563-1574, 1998. In some embodiments cNAP 1 refers to an animal homolog of human cNAP1.

NEK2 refers to the gene encoding (or gene product thereof) NIMA (never in mitosis gene a)-related kinase 2), which, in humans, encodes transcript variants that include the transcript with GenBank Accession No. NM_002497. In some m embodiments ethods NEK2 refers to an animal homolog of human NEK2.

centrin2 refers to the gene encoding (or gene product thereof) EF-hand protein, 2 (CETN2), which, in humans, encodes transcript variants that include the transcript with GenBank Accession No. NM_004344. In some embodiments centrin2 refers to an animal homolog of human centrin2.

CDC14A refers to the gene encoding (or gene product thereof) human homolog A of S. cerevisiae CDC14 cell division cycle 14.

CDC14B refers to the gene encoding (or gene product thereof) human homolog B of S. cerevisiae CDC14 cell division cycle 14.

gapcena refers to the gene encoding (or gene product thereof) RAB GTPase activating protein 1 (RABGAP1), which, in humans, encodes a transcript with GenBank Accession No. NM_012197. In some embodiments gapcena refers to an animal homolog of human gapcena.

Nemo refers to the gene encoding (or gene product thereof) NF-kappaB essential modulator (NEMO), a member of the IκB kinase (IKK) core complex.

IKK1 refers to the gene encoding (or gene product thereof) IKKα subunit of the IκB kinase (IKK) core complex IkappaB kinase (IKK) core complex.

IKK2 refers to the gene encoding (or gene product thereof) IKKβ subunit of the IκB kinase (IKK) core complex IkappaB kinase (IKK) core complex.

Centriolin refers to the gene encoding (or gene product thereof) centrosomal protein 1 (CEP1), which, in humans, encodes a transcript with GenBank Accession No. NM_007018. In some embodiments centriolin refers to an animal homolog of centriolin.

Ninein refers to the gene encoding (or gene product thereof) GSK3B interacting protein, which, in humans, encodes a transcript with GenBank Accession No. NM_182946. In some embodiments ninein refers to an animal homolog of human ninein.

Heat Shock Proteins (HSPs) are found in all cells; they comprise a family of more than 50 different proteins and account for about 5% of total cellular protein. In stressed cells, the percentage of HSPs may increase to 15 or even 20%. The stressors that increase HSPs include physical stresses like excessive heat, chemical stresses like toxins and oxidative conditions, and biological stresses, for example the presence of inflammatory cytokines. The principal functions of HSPs include participation in protein folding and unfolding, protein degradation, and the assembly of multi-subunit complexes. Generally, each centrosome consists of two centrioles (at right angles). Hsp70 and Hsp90 are core components of the centrosome.

Methods of Use

Abnormalities in secretion have been linked to numerous disorders, including diabetes, Huntington's Disease, Alzheimer's Disease, Polycystic Kidney Disease, Addison's Disease, Crohn's Disease. Because of their role in secretion, modulation of centrosomal genes and proteins can be used to treat these disorders at the subcellular level of causation. Secretion in cells can be modulated by, for example, blocking or enhancing the expression of centrosomal genes (e.g., pericentrin, centriolin, δ-tubulin, ε-tubulin, γ-tubulin, GCP2, GCP3, GCP5, cNAP1, PCM1, NEK2, centrin2, CDC14A, CDC14B, gapcena, nemo, IKK1, IKK2), or by, for example, inhibiting or enhancing the activity of, or interfering with the localization of, centrosomal polypeptides (i.e., proteins encoded by centrosomal genes). For example, the new methods can be used to treat these diseases by modulating centrosomal genes (e.g., via RNAi, siRNA, antisense nucleic acids, or ribozymes) in secreting cells so as to increase or decrease secretion in these cells, as necessary. For example, each one of the siRNA molecules of SEQ ID NOs: 1, 3, and 5 can be used effectively to inhibit pericentrin, ε-tubulin, and GCP2, respectively. Inhibiting these genes and proteins results in decreased secretory vesicle storage and increased baseline secretion. Increased expression is expected to result in increased secretory vesicle storage and thus decreased secretion. These and other centrosomal genes can be inhibited individually or in any combination.

In a subject with a secretory disorder these molecules can be delivered to cells in the subject to modulate secretion, thereby ameliorating the symptoms of the disorder and slowing or stopping its progression. Such molecules can be delivered to particular tissues most affected by abnormal secretion, thus localizing the modulatory effects.

In addition, whether or not a cell can secrete proteins will profoundly regulate the transfer of genetic information from the nucleus to the cytoplasm and the structure of its nucleus. Activity of the secretory path is closely tied to the structure and functions of the nucleus. In particular, when "membrane traffic" along the secretory path is interrupted, import of proteins into the nucleus is largely inhibited, and many proteins normally found in the nucleus relocate reversibly to the cytoplasm. These findings may impact the future of research on three genetic diseases—cystic fibrosis, Huntington's disease, and the fragile X syndrome. This is because, in each case, either the secretory path malfunctions or key proteins move between the nucleus and cytoplasm Diabetes/Hyperglycemia In some diabetics, the primary etiology of their disease is decreased insulin secretion. Thus, the methods described herein can be used to identify compounds that modulate insulin secretion. For example, in subjects who suffer from hyperglycemia due to decreased insulin secretion or insulin resistance, but who have intact beta cells capable of secreting insulin, an inhibitor of a centrosomal protein, e.g., an inhibitory nucleic acid as described herein (e.g., an siRNA targeting centriolin, pericentrin, or gamma tubulin) can be administered, to thereby enhance basal levels of insulin secretion.

Huntington's Disease

Huntington's Disease is caused by a single mutated copy of the gene for huntingtin (Htt). The damaged gene makes a version of the protein with an unusually long chain of one of its components, the amino acid glutamine. This mutant Htt forms large inclusion or aggregates. In normal nerve cells, Htt can form a complex with the proteins Hip1. Lengthening the tract of glutamine amino acids in huntingtin weakens this protein's interaction with Hip1 to the extent that it is released. Hip1 then interacts with a newly identified protein, Hippi, that appears to be essential for forming a "death-effector complex" involving caspase-8, thereby setting off the apoptotic cascade. Caspase-3 also cleaves Htt, producing fragments that clump together and form inclusions in the neuron and its nucleus. Thus, molecules that enhance centrosomal proteins, e.g., that increase levels or activity of centrosomal proteins, can be identified by a method described herein for use in the treatment of Huntington's Disease by decreasing the Htt secretion.

Alzheimer's Disease

Alzheimer's Disease is characterized by the abnormal accumulation of amyloid-β peptide and formation of amyloid beta plaques. Thus, molecules that enhance centrosomal proteins, e.g., that increase levels or activity of centrosomal proteins, can be identified by a method described herein for use in the treatment of Alzheimer's Disease.

Polycystic Kidney Disease

Polycystic Kidney Disease is characterized by hypersecretion of fluid-filled vesicles. Thus, molecules that enhance centrosomal proteins, e.g., that increase levels or activity of centrosomal proteins, can be identified by a method described herein for use in the treatment of Polycystic Kidney Disease.

Addison's Disease

Addison's Disease is characterized by insufficiency of adrenal hormones secretion. Thus, molecules that decrease centrosomal proteins, e.g., that decrease levels or activity of centrosomal proteins, can be identified by a method described herein for use in the treatment of Addison's Disease.

Cystic Fibrosis Disease

Cystic fibrosis is a disease of protein transport along the secretory path. A single gene is mutated, and the corresponding cell surface protein normally regulates cellular chloride content, especially in the lungs. In most affected individuals, this protein is made and accumulates along the secretory path without arriving at the cell's surface. Deranged chloride transport leads to thick, viscous secretions in the lungs, pancreas, liver, intestine, and reproductive tract. Thus, molecules that enhance centrosomal proteins, e.g., that increase levels or activity of centrosomal proteins, can be identified by a method described herein for use in the treatment of cystic fibrosis.

Inhibitory Nucleic Acid Molecules

The methods described herein can include the use of inhibitory nucleic acid molecules that are targeted to a selected target RNA coding for a centrosomal protein, e.g., antisense, siRNA, ribozymes, and aptamers.

RNA interference (RNAi)

RNAi is a process whereby double-stranded RNA (dsRNA, also referred to herein as siRNAs or ds-siRNAs, for double-stranded small interfering RNAs) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al., Nat. Biotechnol. 20(5):497-500 (2002); Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism.

Examples of siRNA sequences (along with the target centrosomal gene to be inhibited) that can be used in the new methods include the following (all listed from 5' to 3' (sense) AA-N19-dTdT:

```
                                    (SEQ ID NO:1)
    pericentrin A/B     GCAGCUGAGCUGAAGGAGA (SEQ ID NO:26)
    pericentrin B       UUGGAACAGCUGCAGCAGA
```

-continued

| | |
|---|---|
| δ-tubulin | GGUUCUGGAAACAACUGGG (SEQ ID NO:2) |
| ε-tubulin | AGUCGGCAGAGCACUGUGA (SEQ ID NO:3) |
| γ-tubulin | UGACCGCAAGGACGUCUUU (SEQ ID NO:4) |
| GCP2 | UCUCGUACUCCAGAAGACU (SEQ ID NO:5) |
| GCP3 | AAGAGAAGCAGAUGCUGCA (SEQ ID NO:6) |
| GCP5 | ACUUCGCCUGGUCCAACUU (SEQ ID NO:7) |
| cNAP1 | UCUAUCCGAAAGCCCAGUC (SEQ ID NO:8) |
| PCM1 | GUCCCCAAACAGAGAAAC (SEQ ID NO:9) |
| PCM1 (alternate) | UCAGCUUCGUGAUUCUCAG (SEQ ID NO:10) |
| NEK2 | AGGGAACCAAGGAAAGGCA (SEQ ID NO:11) |
| centrin2 | GAGCAAAAGCAGGAGAUCC (SEQ ID NO:12) |
| CDC14A | GCACAGUAAAUACCCACUA (SEQ ID NO:13) |
| CDC14B | GCAAAUGCUGCCUUCCUUG (SEQ ID NO:14) |
| gapcena | CCAGAGAUGAGCCUACCAG (SEQ ID NO:15) |
| nemo | GAGAUGCCAGCAGCAGAUG (SEQ ID NO:16) |
| IKK1 | ACAGAGAACGAUGGUGCCA (SEQ ID NO:17) |
| IKK2 | UCAGGAAACAGGUGAGCAG (SEQ ID NO:18) |
| Centriolin | GGAUCAGAGACUCUACCUU (SEQ ID NO:19) |
| Ninein | GUGCUGCAGCAGACAUUAC (SEQ ID NO:20) |
| Ninein (alternate) | UAUGAGCAUUGAGGCAGAG (SEQ ID NO:21) |
| CNAP1 (alternate) | CUGUCACUCAAGCCAAGGA (SEQ ID NO:22) |
| siPeri ABS: | GCAGAGAGAUUUAGAGAUUUU (SEQ ID NO:23) |
| siPeri AB: | GGAAAGAGAUCAUGGAGAAUU (SEQ ID NO:24) |
| siPeriBS: | GGAGAGAGAAGGAGCGAGAUU (SEQ ID NO:25) |

In this list of exemplary siRNA sequences, pericentrin A/B siRNA is directed to both pericentrin A and pericentrin B, while pericentrin B siRNA is directed only to pericentrin B (i.e., Kendrin). Sequences designated as "alternate" represent a second exemplary siRNA that can be used to silence the indicated genes in one or more of the methods described herein.

Antisense

An "antisense" nucleic acid can include a nucleotide sequence that is complementary to a "sense" nucleic acid encoding a protein, e.g., complementary to the coding strand of a double-stranded cDNA molecule or complementary to a mRNA sequence encoding a centrosomal protein. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999)).

Target gene expression can be inhibited by targeting nucleotide sequences complementary to a regulatory region (e.g., promoters and/or enhancers) to form triple helical structures that prevent transcription of the Spt5 gene in target cells. See generally, Helene, C. *Anticancer Drug Des.* 6:569-84 (1991);

Helene, C. *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993).

Aptamers

Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al (1992) Nature 355: 564 566 and U.S. Pat. No. 5,582,981 (1996) Toole et al). Methods for selection and preparation of such RNA aptamers are knotn in the art (see, e.g., Famulok, Curr. Opin. Struct. Biol. 9:324 (1999); Herman and Patel, J. Science 287:820-825 (2000)); Kelly et al., J. Mol. Biol. 256:417 (1996); and Feigon et al., Chem. Biol. 3: 611 (1996)).

Administration of Inhibitory Nucleic Acid Molecules

The inhibitory nucleic acid molecules described herein can be administered to a subject (e.g., by direct injection at a tissue site), or generated in situ such that they hybridize with or bind to cellular MRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid nucleic acid molecules to peptides or antibodies that bind to cell surface receptors or antigens. The inhibitory nucleic acid nucleic acid molecules can also be delivered to cells using the vectors described herein. To achieve sufficient intracellular concentrations of the inhibitory nucleic acid molecules, vector constructs in which the inhibitory nucleic acid molecule is placed under the control of a strong promoter can be used.

Pharmaceutical Compositions and Methods of Administration

The therapeutic compounds described herein can be incorporated into pharmaceutical compositions. Such compositions typically include the compound (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with pharmaceutical administration. Supplementary active compounds can also be incorporated into the compositions, depending on the disease to be treated.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the compounds are typically delivered in the form of an aerosol spray from a pressured container or dispenser that contains a suitable propellant, e.g., a gas such as carbon dioxide, or a nebulizer. Such methods include those described in U.S. Pat. No. 6,468,798.

The therapeutic compounds can also be prepared in the form of suppositories (e.g., with conventional suppository bases such as cocoa butter and other glycerides) or retention enemas for rectal delivery.

Therapeutic compounds comprising nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to normal cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

Screening Assays

The methods described herein include screening assays to identify compounds that modulate, i.e., increase or decrease, activity or levels of centrosomal proteins.

Compounds with unknown function can be screened to determine whether they specifically bind to centrosomal genes or the polypeptides they encode, using any standard binding assay. For example, candidate compounds can be bound to a solid support. A centrosomal gene or polypeptide is then exposed to the immobilized compound and binding is measured (e.g., as done in European Patent Application 84/03564). Methods of measuring binding include, for example, enzyme-linked immunosorbent assay (ELISA). ELISAs can be performed using high-throughput methods.

The compounds can also be screened to identify those that increase or decrease levels of centrosomal proteins, e.g., using standard reporter assays. Alternatively, compounds that alter subcellular localization can be identified using fluorescence microscopy.

In some embodiments, the invention provides assays for screening candidate or test compounds that bind to or modulate the activity of a polypeptide encoded by a centrosomal gene, or biologically active portion of that polypeptide. The test, or "candidate," compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, Anticancer Drug Des., 12:145, 1997).

Examples of methods useful for the synthesis of molecular libraries can be found in the art (e.g., DeWitt et al., Proc. Natl. Acad. Sci. USA, 90:6909, 1993; Erb et al., Proc. Natl. Acad. Sci. USA, 91:11422, 1994; Zuckermann et al., J. Med. Chem., 37:2678, 1994; Cho et al., Science, 261:1303, 1993; Carrell et al., Angew. Chem. Int. Ed. Engl., 33:2059, 1994; Carell et al., Angew. Chem. Int. Ed. Engl., 33:2061, 1994; and Gallop et al., J. Med. Chem., 37:1233. 1994).

Libraries of compounds can be presented in solution (e.g., Houghten, Bio/Techniques, 13:412-421, 1992), or on beads (Lam, Nature, 354:82-84, 1991), chips (Fodor, Nature, 364:555-556, 1993), bacteria (U.S. Pat. No. 5,223,409), spores (U.S. Pat. Nos. 5,571,698; 5,403,484; and 5,223,409), plasmids (Cull et al., Proc. Natl. Acad. Sci. USA, 89:1865-1869, 1992) or phage (Scott and Smith, Science, 249:386-390, 1990; Devlin, Science, 249:404-406, 1990; Cwirla et al., Proc. Natl. Acad. Sci. USA, 87:6378-6382, 1990; and Felici, J. Mol. Biol., 222:301-310, 1991).

In some embodiments, an assay is a cell-free assay in which a purified and/or recombinant centrosomal polypeptide, or a biologically active portion thereof, is contacted with a test compound and the ability of the test compound to bind with the polypeptide is determined. Determining the ability of the test compound to bind with the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a centrosomal polypeptide, or a biologically active portion thereof, with a known compound that binds to the polypeptide to form an assay mixture, contacting the assay mixture with a test compound, and determining the ability of the test compound to interact with the centrosomal polypeptide, wherein determining the ability of the test compound to interact with the centrosomal polypeptide includes determining the ability of the test compound to preferentially bind with the centrosomal polypeptide or a biologically active portion thereof as compared to the known compound.

In some embodiments, the assay involves assessment of an activity characteristic of the polypeptide, wherein binding of the test compound to the centrosomal polypeptide or a biologically active portion thereof alters (i.e., increases or decreases) the activity of the polypeptide. In general, in the methods described herein, the activity is cellular secretion. Thus, the methods can include determining whether a candidate compound affects cellular secretion in a desirable manner, using assays known in the art and described herein.

EXAMPLES

The invention is further described in the following examples, which do not limit the scope of the invention described in the claims.

Example 1

Pericentrin and γ-Tubulin Localize to the Centrosome and Granules in Secretory Cells of Pancreatic Islets and in MIN6 Cells The cytosolic localization of pericentrin and γ tubulin was determined in non-dividing cells of pancreatic islets and acinar cells and contrasted with the dividing pancreatic β cell line MIN6, as well as primary fibroblasts. Pericentrin showed the expected centrosome localization with cytoplasmic 'haze' in primary fibroblasts (FIG. 1A, fibroblast pseudo colored in red, fibroblast enlargement to the right, arrow-centrosome). Conversely, pericentrin in isolated pancreatic islet cells showed additional speckle-like staining (FIG. 1A, B, enlargement, arrowheads-cytoplasmic speckles) in addition to the centrosome staining (FIG. 1B, enlargement, arrows-centrosome). Pancreatic tissue sections showed centrosome staining in acinar cells and centrosome and granular staining in the islet (FIG. 1C, centrosome-arrow, granules-arrowheads). Pericentrin granular staining seemed to be more abundant in the endocrine cells of the islet and much weaker in the acinar exocrine cells in the pancreatic section. The localization of proinsulin and insulin in the pancreatic tissue sections was also compared; the results indicated that the colocalization of pericentrin and proinsulin (FIG. 1D) was not as strong as the colocalization with the antibody that recognized both mature and immature insulin (FIG. 1C). Therefore, pericentrin seemed to be colocalized with mature insulin in the pancreatic islet. When the localization of pericentrin in other endocrine secretory cells of the islet was compared, pericentrin was found to be colocalized with glucagon-secreting cells (FIG. 1E), as well as somatostatin- and pancreatic polypeptide-secreting cells. Thus, pericentrin seemed to be globally expressed in the secretory cells of the pancreatic islet.

In order to determine if centrosomal protein localization to the secretory cells was specific to pericentrin, the localization of another integral centrosome protein, γ tubulin, was investigated in the commonly used mouse insulinoma cell line MIN6. Immunofluorescence staining for γ tubulin in the β cell line showed a granular localization in addition to that at the centrosome (FIG. 1F, arrow-centrosome, arrowheads-cytoplasmic granules).

This indicates that the granular localization of centrosome proteins may be a general phenomenon of endocrine secretory cells.

Example 2

Figures 2A, 2B, 2C, 2D, 2E, 2F, 2G, 2H, 2I:
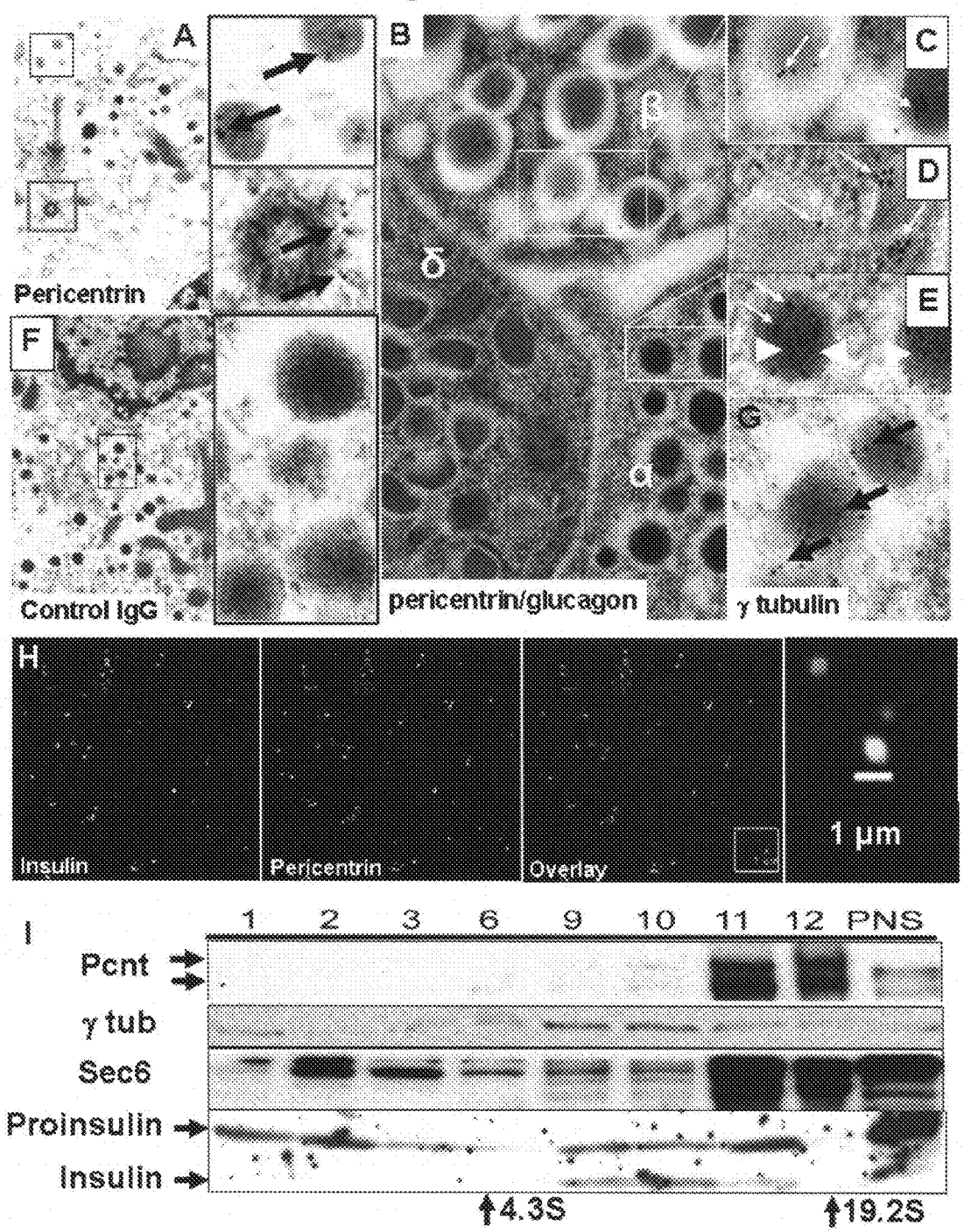
FIGS. 2A-G are immunoelectron microscopy images of isolated pancreatic islets labeled with pericentrin (2A-E), control IgG (2F), and γ tubulin (2G) primary antibodies and visualized with the appropriate gold-labeled secondary antibody. Insets in panel A were enlarged to show pericentrin staining on secretory granules black box) and a centrosome (red box). Pericentrin labeled secretory granules of β (2C), δ (2D), and α (2E) cells. α cells were verified by anti-glucagon staining (2E, arrowheads). Secretory granules were also labeled with γ tubulin antibody (2G), but not with control IgG (2F and inset).
FIG. 2H is a fluorescence image of the results of microcentrifugation fractionation of Min6 cells. The fraction predicted to contain insulin secretory granules was spun onto coverslips and immunostained for insulin and pericentrin, with overlay in yellow (3rd panel). Enlargement of inset (4th panel) shows the granules are less than 1 μm in size, consistent with the size of insulin granules (0.5-0.8 μm).
FIG. 2I shows the results of an Iodixinol density gradient of Min 6 cells. Aliquots of postnuclear supernatants (PNS) and gradient fractions were analysed by immunoblotting with pericentrin (Pcnt), γ tubulin (γ tub), Sec6, and insulin antibodies. Fraction numbers are shown at the top; arrows indicate calculated gradient density in Svedberg units. The experiment was repeated four times with similar results.

Centrosome Proteins Localize to Insulin Granules and Co-Migrate with Insulin on an Iodixinol Density Gradient Electron microscopy revealed that pericentrin and γ tubulin staining is confined to electron dense material surrounding the centrioles and primary cilium (FIG. 2A, enlargement in bottom (red) box, arrows—5 nm gold particles) and to the insulin secretory granules (FIG. 2A, enlargement in top (black) box; 2B, enlargements 2C and 2G, arrows). Pericentrin immmuno-gold staining was also present in the α and δ cells of the pancreatic islet (FIG. 2B, enlargements 2D-E, arrows—10 nm gold). The glucagon immuno-gold staining (5 nm) was specific to α cells (FIG. 2E, arrowheads—5 nm gold). Pericentrin controls included rabbit IgG which showed no specific staining (FIG. 3F, enlargement at right) in addition to insulin, glucagon and somatostatin antibody showing specific staining for their corresponding secretory granules (FIG. 2E, and additional data not shown).

In order to further verify that pericentrin and γ tubulin associate with secretory granules, microcentrifuge based cell fractionation was performed in MIN6 cells (Miyazaki et al., Endocrinology. 127(1):126-32 (1990)). Biochemical analysis of insulin granules using iodixanol density gradient was performed as described in Buchanan et al, Biochem J., 360(Pt 2):431-9 (2001). Briefly, the cells were homogenized, then the homogenate was centrifuge at 500 g for 10 minutes. The post-nuclear supernatant (PNS) was layered onto a 8-19% iodixanol gradient, which was then centrifuged at 160,000 g for 16 hours. The fractions were collected from the top, and Western analysis was performed.

Pericentrin was again shown to co-localize with insulin positive granules by immunofluoresence imaging (FIG. 2H, enlargement in last panel). Moreover, as shown in FIG. 2I, pericentrin and γ tubulin were shown to co-migrate with insulin and Sec6 (FIG. 2I), a member of the exocyst complex, an evolutionarily conserved complex that was shown to co-localize with insulin and to be important for insulin secretion (Tsuboi et al., J. Biol. Cell. 280(27):25565-70 (2005)).

The presence of these centrosomal proteins on insulin secretory granules is indicative of a role for these proteins in insulin secretion.

Example 3

Pericentrin Depletion Decreases Insulin Granules in MIN6 Cells

Figures 3A, 3B, 3C, 3D, 3E:
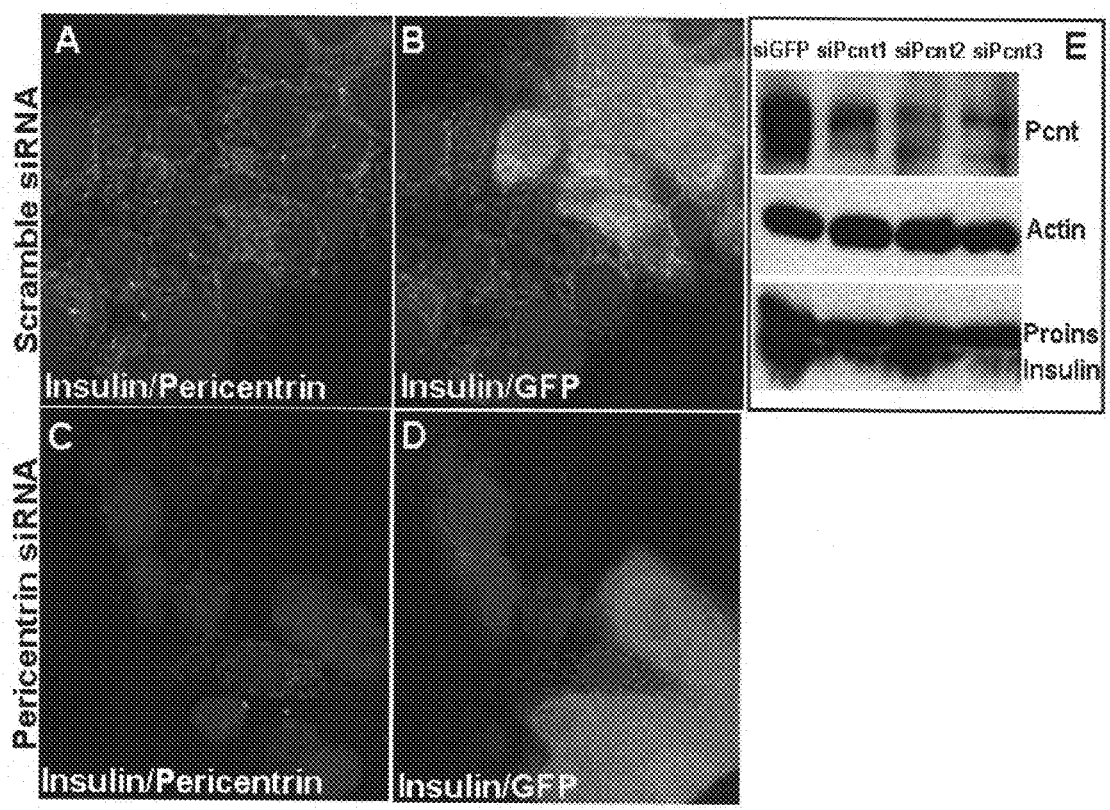
FIGS. 3A-D are photomicrographs showing that pericentrin depletion disrupts insulin secretory granules. MIN6 cells were placed in culture and co-transfected with siRNA and a GFP plasmid as a marker for transfected cells. After 72 hrs, cells were immunostained with pericentrin and insulin antibodies. Top panels show cells co-transfected with a control (scrambled) siRNA and GFP and labeled for (3A) insulin (red) and pericentrin (green). The same cells (3B) showed no loss of insulin granules (red) with GFP transfection (green). In contrast, cells co-transfected with pericentrin siRNA and GFP (bottom panels) show (3A) reduced staining of pericentrin (green) and a decrease in insulin staining (red). The same cells (3D) show reduced insulin staining (red) only in GFP-transfected cells (green).
FIG. 3E shows the results of immunoblot analyses demonstrate knockdown of pericentrin (Pcnt) expression with 3 different pericentrin siRNAs. Intracellular insulin expression, particularly mature insulin, was decreased with pericentrin knockdown relative to control. Actin was used to demonstrate equal loading of protein.

Pericentrin was successfully depleted by three different, specific siRNAs in MIN6 insulinoma cells (FIG. 3E). Scrambled siRNA was used for control. Immuno-fluorescence microscopy revealed that pericentrin knockdown significantly decreased insulin granules as compared to scrambled siRNA treated cells (FIG. 3A-D). Western analysis also showed a decrease in the amount of mature insulin in MIN6 cells (FIG. 3E).

These results demonstrate that pericentrin siRNA depletes insulin granules in the MIN6 insulinoma cell line.

Example 4

Figures 4A, 4B, 4C, 4D, 4E, 4F:
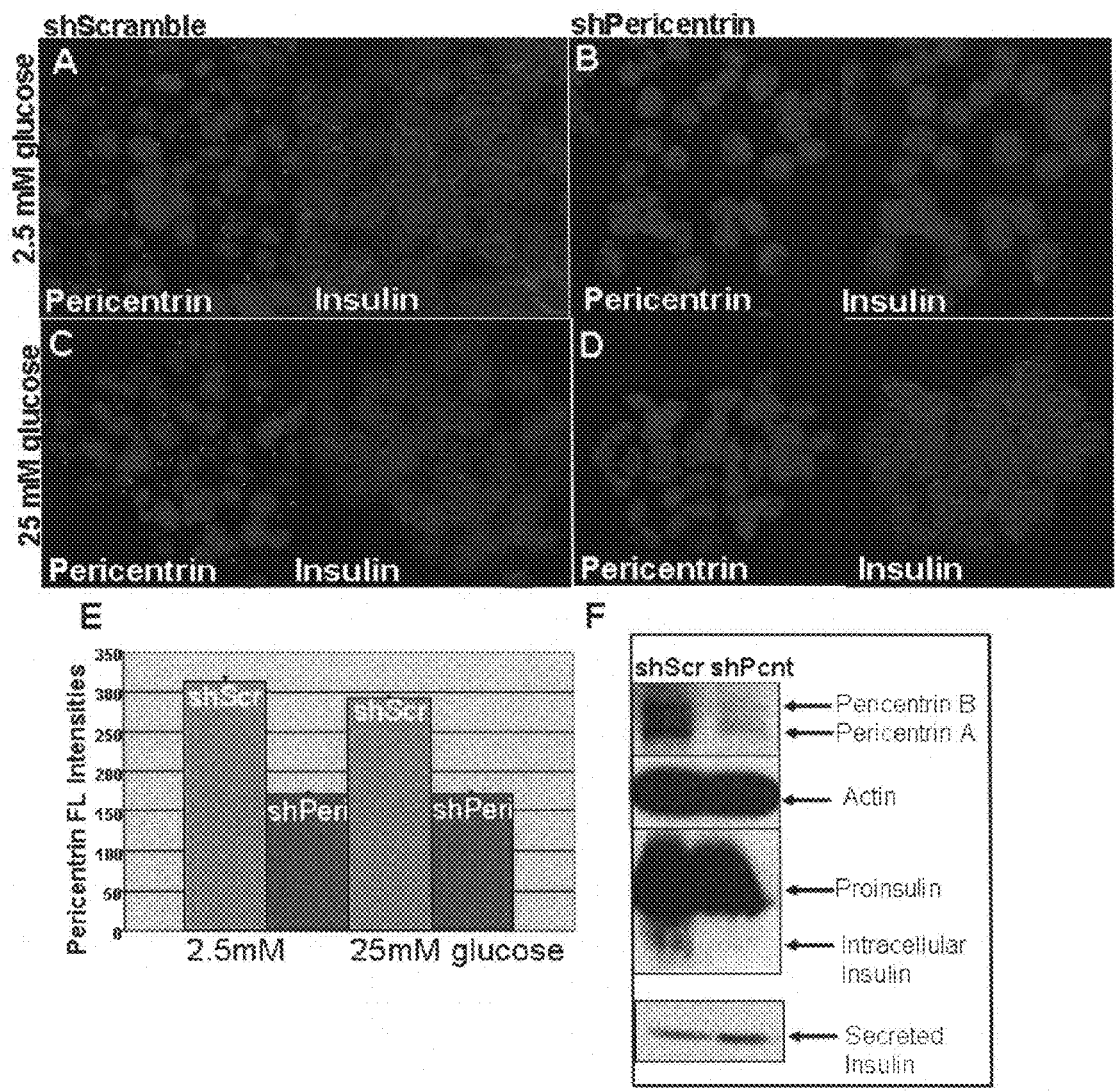
FIGS. 4A-D are photomicrographs showing that pericentrin depletion of insulin granules can be rescued by stimulation of insulin synthesis with high glucose. MIN6 insulinoma cells were stably transduced with lentivirus (LV) shRNAs against pericentrin or control (scrambled). The stable cell lines were transferred into low glucose media (2.5 mM) for 1 hour (4A-B), followed by incubation in high glucose media (25 mM) for an additional 1 hour (4C-D). Immunofluorescence imaging revealed typical staining for pericentrin (green) and insulin (red) in cells transduced with scrambled shRNA (left panels), either in low or high glucose. Depletion of pericentrin with shRNA (4B) caused a reduction in pericentrin staining (green) and a decrease in intracellular insulin following incubation in low glucose media. However, following stimulus with high glucose for 1 hour (4D), the cells were able to refill their insulin granule content.
FIG. 4E is a bar graph showing the results of fluorescence quantitation of pericentrin immunostaining following transduction with LV-scrambled shRNA or LV-pericentrin shRNA and incubation in low or high glucose.
FIG. 4F shows the results of immunoblotting for pericentrin in cells transduced with LV-scrambled shRNA or LV-pericentrin shRNA. Intracellular insulin expression, particularly mature insulin, was decreased with pericentrin knockdown relative to control. Extracellular insulin secreted into the media is elevated by pericentrin depletion. Actin is shown as a loading control.
Figure 4G:
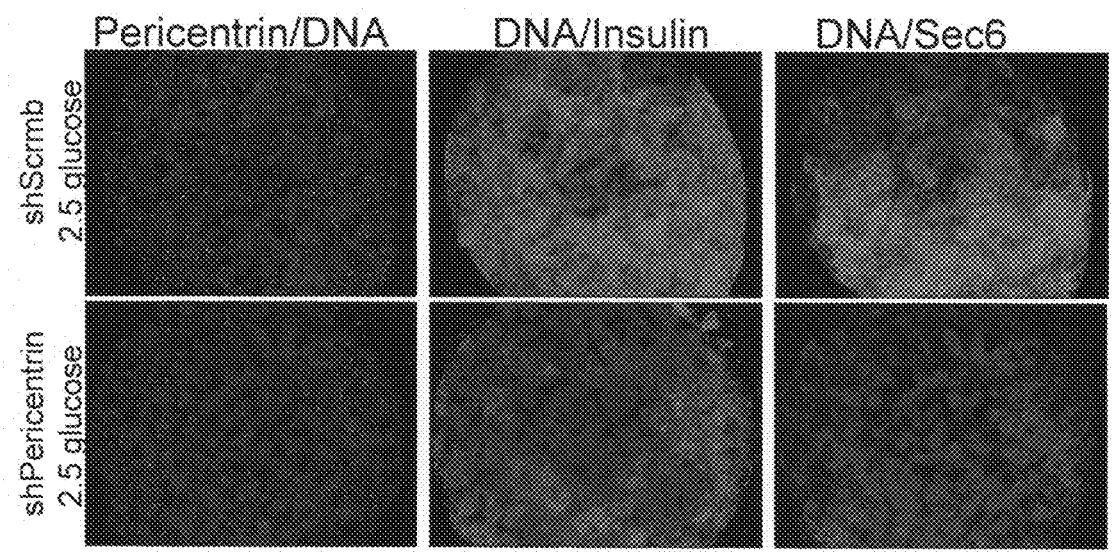
FIG. 4G is a set of six fluorescence photomicrographs showing that pericentrin depletion in mouse islets decreases intracellular insulin granules and sec6 levels at low (2.5 mM) glucose concentrations. Islets were transduced with lentivirus (LV) shRNAs against pericentrin (bottom row) or control (scrambled, top row), and stained for pericentrin (left column), insulin (middle column), or sec6 (right column). Each image also shows counterstaining for DNA (blue), identifying the nuclei of individual cells.
Figure 4H:
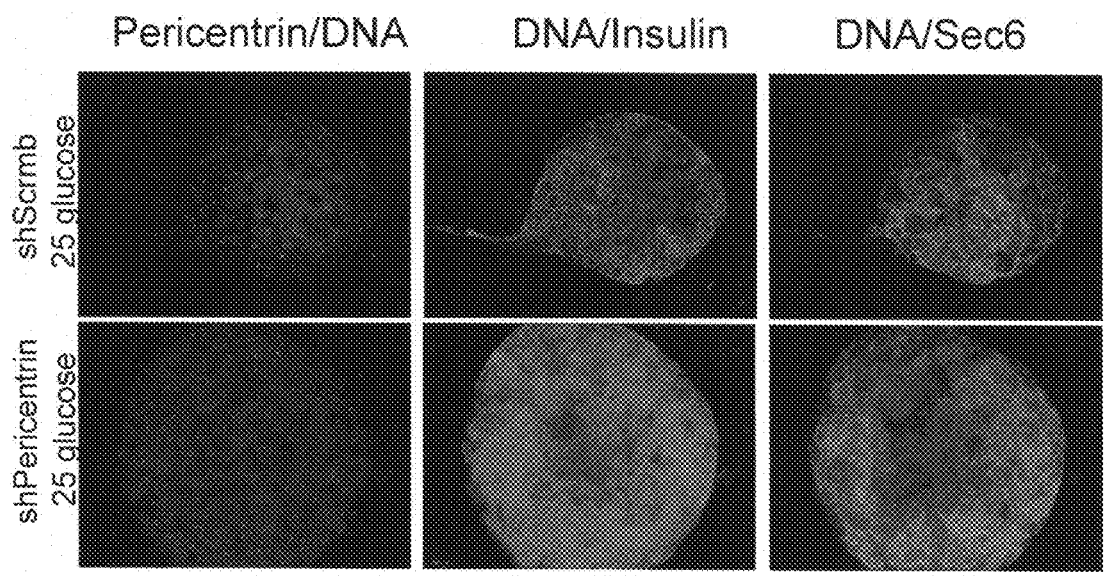
FIG. 4H is a set of six fluorescence photomicrographs showing that pericentrin depletion does not affect insulin biosynthesis in mouse islets in high (25 mM glucose). Islets were transduced with lentivirus (LV) shRNAs against pericentrin (bottom row) or control (scrambled, top row), and stained for pericentrin (left column), insulin (middle column), or sec6 (right column). Each image also shows counterstaining for DNA (blue), identifying the nuclei of individual cells.

Pericentrin Knockdown-Induced Insulin Depletion Can Be Rescued by Glucose Stimulated Insulin Production Pericentrin was depleted using a lentivirus mediated shRNA system in MIN6 cells and islets (FIGS. 4A-H). In order to show that pericentrin depletion of insulin granules is not simply due to non-specific toxic effects to the cells, glucose stimulation experiments were performed. After pericentrin was stably depleted by shRNA we transferred the insulinoma cells into low glucose media (2.5 mM glucose) in order to bring them to baseline before stimulations. After 1 hour incubation at low glucose the media was replaced with high glucose media (25 mM) for 1 hour and immunofluorescence imaging was performed on the cells. As previously shown, pericentrin depletion caused a decrease in the intensity of insulin granule immunofluorescence in the initial state of low glucose media (FIG. 4B). However, after incubation in high glucose for 1 hour the cells were able to refill their insulin granule content (FIG. 4D).

Thus, these experiments show that pericentrin depletion degranulates the cells, probably by causing constitutive secretion of insulin without storage. Thus, it is likely that pericentrin and other centrosome proteins are structural components of insulin secretory granules.

Example 5

Pericentrin Knockdown Causes Degranulation of f Cells of Pancreatic Islets

Figures 5A, 5B, 5C, 5D:
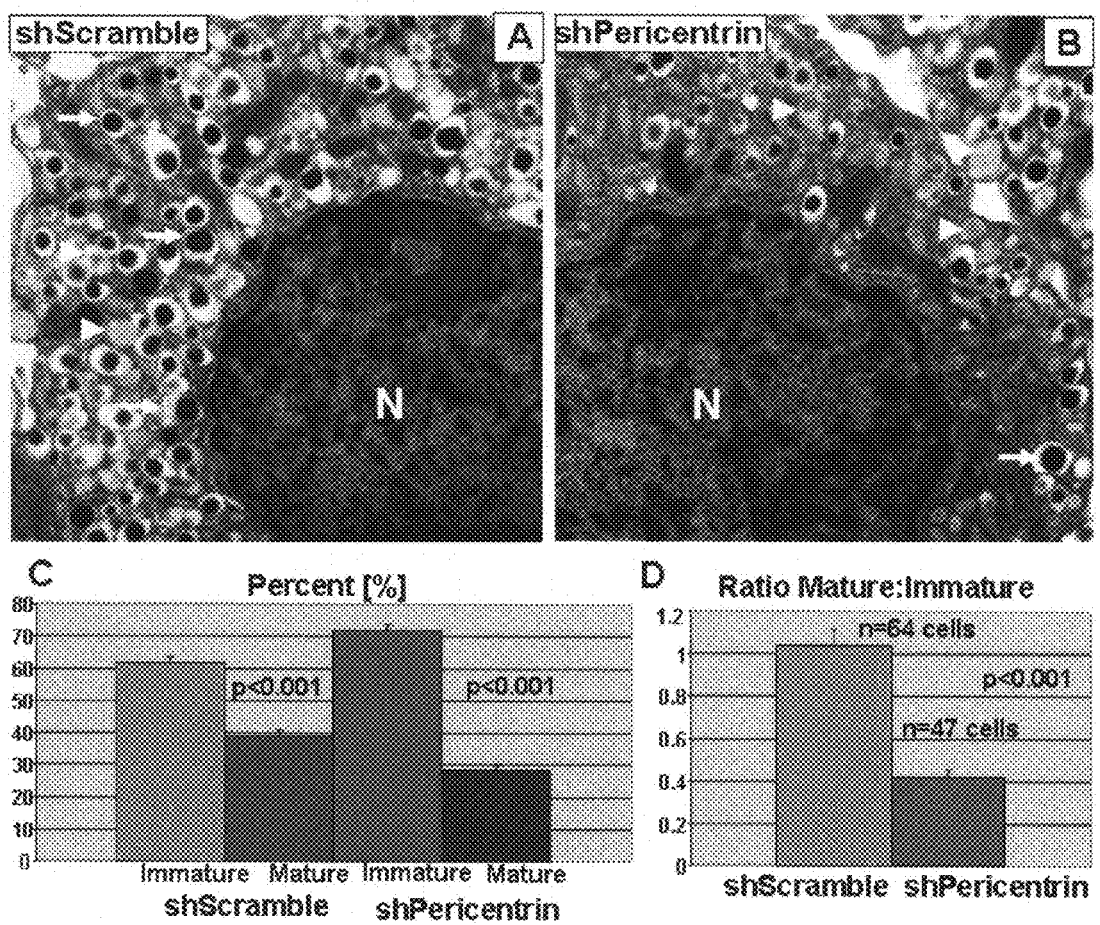
FIGS. 5A-B are electron micrographs (top panels) of pancreatic islet cells transduced with scrambled (5A) or pericentrin (5B) shRNAs. The cells were fixed in glutaraldehyde and sectioned for cellular morphology. Normal, electron dense secretory granules (white arrows) and less dense, immature granules (white arrowheads) are shown. N, nucleus.
FIG. 5C is a bar graph showing the results of quantitation of granules showed a significant decrease in the number of mature granules and increase in the number of immature granules in pericentrin shRNA treated islets.
FIG. 5D is a bar graph showing that the ratio of mature to immature granules in pericentrin shRNA treated cells. Mature and immature granules were counted in number of randomly selected cells from each group by a person unaware of the treatment status. These results indicate that pericentrin knockdown causes degranulation of β cells in the pancreatic islet.

In order to further characterize which insulin granules we were losing in pericentrin depleted cells EM analysis on shPericentrin or shScrambled treated islets was performed. The results indicated that the mature dense core insulin granules seem to be preferentially lost in pericentrin depleted islets (FIGS. 5A-B, arrows). The immature, proinsulin granules were less affected (FIGS. 5A-B, arrowheads). Moreover, the ratio of mature to immature granules per β cell is significantly decreased by pericentrin depletion (FIG. 5C).

This indicates that pericentrin knockdown causes a decrease in mature insulin granules either by hypersecretion of the mature granules or by inhibition of maturation of the immature granules.

Example 6

Depletion of Pericentrin in Pancreatic Islets Causes Misregulation of Insulin and Glucose Intolerance in Vivo To determine if pericentrin knockdown has an effect on insulin secretion in vivo, shPericentrin and shScrambled treated islets were transplanted into streptozotocin treated balb/c mice under the kidney capsule, and glucose tolerance tests were performed. Briefly, streptozotocin was administered to 6-8 week old mice to induce beta cell loss and diabetes. Blood glucose (BG) levels were monitored to confirm the development of diabetes. Two weeks later, islet cells were obtained from donor mice and cultured overnight in the presence of lentiviral vectors carrying pericentrin shRNA or scrambled control shRNA. The next day, the donor shRNA-treated islets were transplanted under the kidney capsule of the recipient mice.

Alternatively, shPericentrin and shScrambled treated and sorted Min6 cells were transplanted under the skin.

Figure 6A:
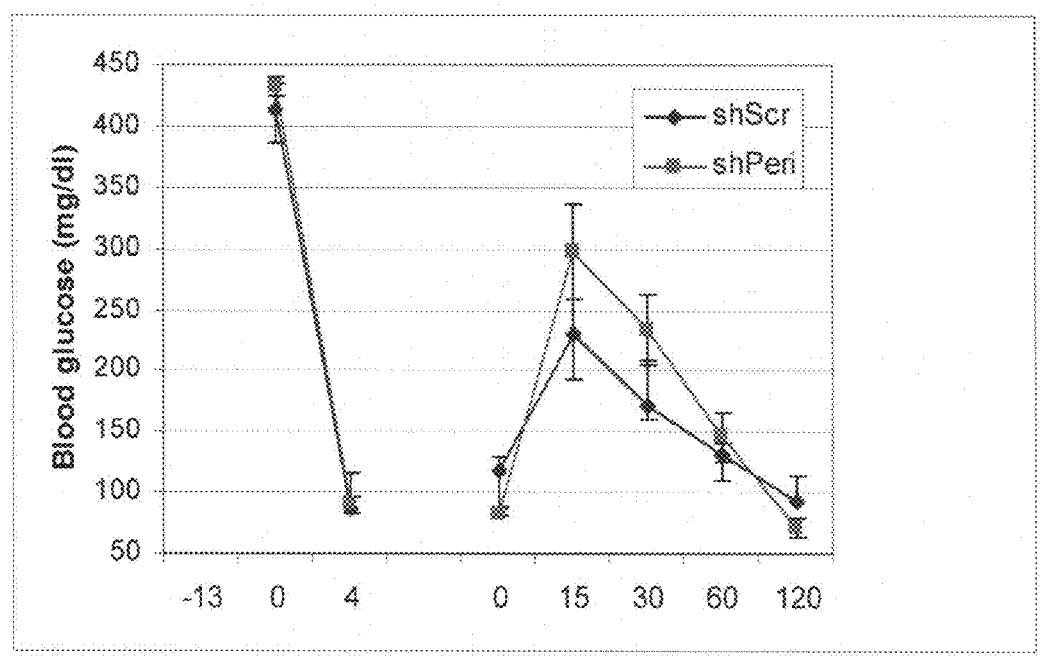
FIGS. 6A-6B are bar graphs showing the results of experiments in which a streptozotocin-induced diabetic recipient mice were transplanted with (6A) syngeneic islets which were previously transduced for 18 hours in culture with lentivirus control (scrambled) or pericentrin shRNA vectors or (6B) Min6 transduced and sorted shPericentrin and shScrambled cells. After the indicated days of transplantation, the mice were fasted overnight and then given a glucose tolerance test. Blood sugars were determined at the days and times shown. These results indicate that pericentrin knockdown causes dysregulation of insulin secretion in vivo.
Figure 6B:
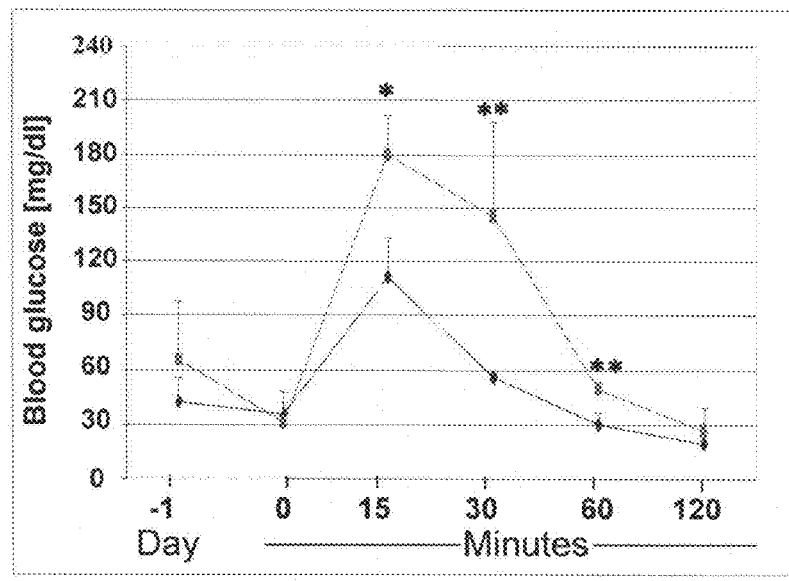

Both pericentrin and scrambled shRNA treated islets and cells were able to restore normal blood glucose in diabetic mice (FIG. 6A, islets, 6B, Min6 cells). After overnight fasting, the pericentrin depleted mice had significantly lower blood glucose as compared to scrambled mice consistent with insulin hypersecretion (FIG. 6A). Overnight fasting could not be performed with the mice that received insulinoma cells, since their blood glucose was already very low. Therefore, those animals were fasted for only 5 hours before the glucose tolerance. After IP insulin bolus pericentrin depleted mice initially had higher blood glucose indicating that their islets were degranulated after hypersecretion.

During the subsequent time points, pericentrin knockdowns were able to secrete insulin at the higher rate than scrambled controls, consistent with the high glucose-induced refill of the insulin granules in vitro (e.g., as shown in FIGS. 4A-F).

These results indicate that centrosomal proteins, e.g., pericentrin, play a role in regulating secretion of insulin granules, and a reduction in centrosomal protein levels results in a dearth of stored, mature insulin granules and increased levels of constitutive secretion.

Example 7

Figures 7A, 7B, 7C:
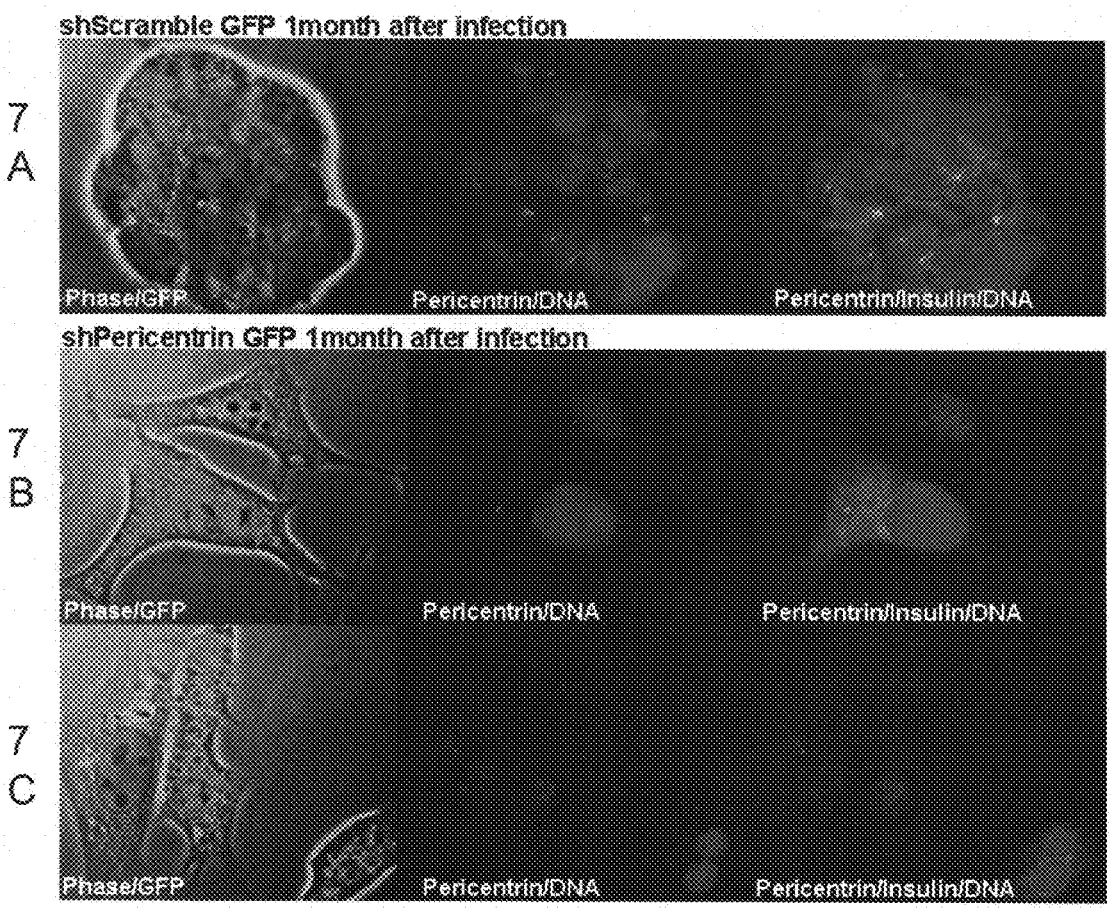
FIGS. 7A-C are each rows of three photomicrographs of MIN6 insulinoma cells that were stably transduced and GFP sorted for one month with LV shRNAs against pericentrin or control (scrambled).

Prolonged Depletion of Pericentrin Causes Total Loss of Insulin Productive Capability in the Min6 Cells To determine the effect of prolonged pericentrin depletion, Min6 cells were stably transduced with shpericentin or shScrambled shRNA co-expressing GFP plasmid. The GFP positive cells were FACS sorted and cultured in normal growth media. After one month a progressive loss of insulin was observed in the pericentrin shRNA transduced cells as compared to the normal insulin levels in the scrambled control (FIGS. 7A-C). Moreover, the morphology of the pericentrin knockdown cells was tremendously different from the scrambled control. Based on the actin and microtubule cytoskeleton, the pericentrin depleted cells became flatter, appeared to have de-differentiated, and no longer produced insulin.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of identifying a candidate modulator of insulin secretion, the method comprising:
    providing a cell that expresses pericentrin;
    contacting the cell with a test compound;
    detecting an effect of the test compound on levels of expression of pericentrin; and
    identifying the test compound as a candidate modulator of insulin secretion if the test compound increases or decreases expression of pericentrin.

2. The method of claim 1, wherein the cell is an insulin-secreting cell.

3. The method of claim 2, wherein the insulin-secreting cell is a pancreatic beta cell.

4. The method of claim 2, wherein the insulin-secreting cell is a MIN6 cell.

5. The method of claim 1, wherein the test compound is a small molecule.

6. The method of claim 1, wherein the test compound is an inhibitory nucleic acid.

7. The method of claim 1, further comprising evaluating an effect of the test compound on insulin secretion in an insulin-secreting cell, wherein a test compound that has an effect on insulin secretion in the insulin-secreting cell is identified as a modulator of insulin secretion.

8. The method of claim 7, wherein the insulin-secreting cell is a pancreatic beta cell.

9. The method of claim 7, wherein the insulin-secreting cell is a MIN6 cell.

10. An in vitro method of identifying a candidate modulator of insulin secretion, the method comprising:
    providing a cell expressing a reporter construct comprising a pericentrin promoter linked to a reporter gene, such that expression of the reporter gene is indicative of expression driven by the pericentrin promoter;
    contacting the cell with a test compound;
    detecting an effect of the test compound on levels of expression of the reporter gene; and
    identifying the test compound as a candidate modulator of insulin secretion if the test compound increases or decreases expression of the reporter gene.

11. The method of claim 10, wherein the cell is an insulin-secreting cell.

12. The method of claim 11, wherein the insulin-secreting cell is a pancreatic beta cell.

13. The method of claim 11, wherein the insulin-secreting cell is a MIN6 cell.

14. The method of claim 10, wherein the test compound is a small molecule.

15. The method of claim 10, wherein the test compound is an inhibitory nucleic acid.

16. The method of claim 10, further comprising evaluating an effect of the test compound on insulin secretion in an insulin-secreting cell, wherein a test compound that has an effect on insulin secretion in the insulin-secreting cell is identified as a modulator of insulin secretion.

17. The method of claim 16, wherein the insulin-secreting cell is a pancreatic beta cell.

18. The method of claim 16, wherein the insulin-secreting cell is a MIN6 cell.

19. An in vitro method of identifying an agent that modulates insulin secretion in a cell, the method comprising:
    selecting a test compound on the basis that it increases or decreases expression levels of a pericentrin;
    providing an insulin-secreting cell that expresses pericentrin;
    contacting the cell with the test compound;
    evaluating an effect of the test compound on insulin secretion in the cell; and
    identifying the test compound as an agent that modulates insulin secretion if the test compound has an effect on insulin secretion in the cell.

20. The method of claim 19, wherein the insulin-secreting cell is a pancreatic beta cell.

21. The method of claim 19, wherein the insulin-secreting cell is a MIN6 cell.

22. The method of claim 19, wherein the test compound is an inhibitory nucleic acid.

23. The method of claim 19, wherein the test compound is an inhibitory nucleic acid.

* * * * *

UNITED STATES PATENT AND TRADEMARK OFFICE
CERTIFICATE OF CORRECTION

| | |
|---|---|
| PATENT NO. | : 7,972,803 B2 |
| APPLICATION NO. | : 11/985545 |
| DATED | : July 5, 2011 |
| INVENTOR(S) | : Agata Jurczyk et al. |

It is certified that error appears in the above-identified patent and that said Letters Patent is hereby corrected as shown below:

Column 30, line 23, "of a pericentrin" should be changed to --of pericentrin--.

Signed and Sealed this
Thirteenth Day of September, 2011

David J. Kappos
*Director of the United States Patent and Trademark Office*